United States Patent [19]

Colescott et al.

[11] 4,242,238

[45] Dec. 30, 1980

[54] SYNTHESIS OF PEPTIDES

[75] Inventors: Robert L. Colescott, Bourbonnais; Emil Kaiser, Chicago; Charles D. Bossinger, Olympia Fields, all of Ill.

[73] Assignee: Armour and Company, Phoenix, Ariz.

[21] Appl. No.: 657,753

[22] Filed: Feb. 13, 1976

[51] Int. Cl.³ .................... C08L 37/00; C07C 103/52; A61K 37/00
[52] U.S. Cl. ................ 260/8; 260/112.5 R; 424/177
[58] Field of Search ............ 260/112.5 R, 8; 424/177

[56] References Cited

U.S. PATENT DOCUMENTS

| | | | |
|---|---|---|---|
| 3,912,711 | 10/1975 | Leeman et al. | 260/112.5 R |
| 3,915,949 | 10/1975 | Colescott et al. | 260/112.5 R |
| 3,917,579 | 11/1975 | Bumpus et al. | 260/112.5 R |
| 3,926,938 | 12/1975 | Hughes et al. | 260/112.5 R |
| 3,987,014 | 10/1976 | Guiducci et al. | 260/112.5 R |
| 3,988,307 | 10/1976 | Gross | 260/112.5 R |
| 4,002,740 | 1/1977 | Goldstein et al. | 260/112.5 R |
| 4,022,760 | 5/1977 | Tinney | 260/112.5 R |

OTHER PUBLICATIONS

Bajusz et al., Chem. Abstr. 71:77857h (1969).
Laslo et al., Chem. Abstr. 75:905x (1971).
Pekkarinen et al., Chem. Abstr. 70:538b (1969).
Bruckner et al., Chem. Abstr., 72:3777f (1970).
J. M. Stewart and J. D. Young, "Solid Phase Peptide Synthesis", Freeman and Co., San Francisco, 1969, pp. 1–5, 19, 20.

*Primary Examiner*—Delbert R. Phillips
*Attorney, Agent, or Firm*—Carl C. Batz

[57] ABSTRACT

Resin peptides useful in preparing peptides having biological activity, and particularly such resin peptides containing ALA-GLU-$CH_2$-Ⓡ at one end of an amino acid chain, Ⓡ being the resin and ALA and GLU being the residues of the amino acids alanine and glutamic acid; and processes for the preparation of such resin peptides. Resin peptides including ACTH$^{1-28}$ are disclosed which have adrenocorticotropic activity along with processes for their preparation.

6 Claims, No Drawings

SYNTHESIS OF PEPTIDES

This invention relates to the synthesis of peptides and particularly to resin peptides which are biologically active or which are useful in the preparation of biologically active peptides. The invention involves such peptides as new compounds and also processes for their preparation.

BACKGROUND

It has long been known that certain naturally biologically active substances can be obtained from the glands of animals and the substances so obtained utilized in the treatment of deficiencies of the human body. One such substance is adrenocorticotropic hormone, commonly called ACTH, which may be obtained from the pituitary glands of animals.

The burden of having to collect the relatively small pituitary glands of animals, and the tedious processes involved in their extraction to obtain only a small amount of active material, made it desirable to discover practical methods for synthesizing the biologically active substances.

We are aware of disclosures of certain laboratory methods for the synthesis of certain peptides of relatively short amino acid chain lengths. These include an article by R. B. Merrifield entitled "Solid Phase Peptide Synthesis I. The Synthesis of a Tetrapeptide" at pages 2149 to 2154 in Vol. 85 of Journal of the American Chemical Society (1963) and a book entitled "Solid Phase Peptide Synthesis" by John W. Stewart and Janis D. Young published by W. H. Freemand and Company of San Francisco, California.

In our U.S. Pat. No. 3,915,949 dated Oct. 28, 1975 we set forth practical methods by which the hormone ACTH may be synthesized. This substance includes a chain of 39 amino acid residues in a certain prescribed sequence. In this synthesis of the biological substance each of the amino acid moieties have to be added to a molecular structure one at a time and in a certain sequence, and each of such reactions contribute to the chance for errors which may accumulate to ruin the product or seriously affect its efficacy.

Accordingly, we have attempted to synthesize new substances having shorter amino acid chain lengths which are as active biologically or which may be even more active than substances previously known, and have sought ways for preparing such substances. Further, we have sought new methods and new intermediates which facilitate the preparation of the new biologically active substances.

SUMMARY

We have discovered a substance having a chain of 28 amino acids which has biological activity as an andrenocorticotropic hormone, and have further discovered intermediate compounds having shorter amino acid chain lengths which are useful in the preparation of this substance and may be useful in the preparation of other active substances. We have also discovered practical processes for the preparation of these substances and the intermediate compounds.

DESCRIPTION

In general, we utilize in our synthesis a solid phase procedure whereby an insoluble crosslinked resin obtained by catalytic polymerization of styrene and divinyl benzene is chlorinated.

To the chlorinated resin, we couple first glutamic acid, then alanine and then the other amino acids of the chain, in prescribed sequence, using a system of protection and deprotection of the active amino and carbonyl groups. Following the coupling of the last amino acid in the chain, the resin is cleaved from the peptide chain and the remaining protective groups removed. In this specific description all amino acids are the naturally occurring L-isomers unless otherwise stated.

In this synthesis the functional groups of the amino acids are protected by blocking groups. The α-amino group of the amino acids is protected by a tertiary butylloxycarbonyl group or an equivalent thereof. This tertiary butyloxycarbonyl group we designate as BOC.

The hydroxyl functions of serine are protected by a benzyl or benzyl derivative group such as 4-methoxybenzyl, 4-methylbenzyl, 3, 4-dimethylbenzyl, 4-nitrobenzyl, benzhydryl or an equivalent thereof. We use the term Bz to represent this benzyl or benzyl derivative group.

The hydroxyl function of tyrosine may be unprotected or may be protected by a Bz group as above described, or may be protected by a benzyloxycarbonyl or a benzyloxycarbonyl derivative such as 2-chlorobenzyloxycarbonyl or a 2-bromobenzyloxycarbonyl group or the equivalent thereof. We use the term Y to represent either no protective group, a Bz group, a benxyloxycarbonyl group or a benzyloxycarbonyl derivative group.

The guanidino function of arginine may be protected by a nitro group, a tosyl group or an equivalent thereof. We use the character T to represent either a nitro group or a tosyl group or the equivalent thereof.

Where lysine is attached we prefer to use as the ε-amino protection agent trifluoroacetyl(TFA) but may also use carbobenzyloxy (CBZ), 2-chlorocarbobenzyloxy (Cl-CBZ), 2-bromocarbobenzyloxy, 2,4-dichlorocarbobenzyloxy. We use the symbol V to represent such a group.

The amide function of asparagine may be unprotected or may be protected by an xanthydryl or a benzhydryl group. We use the character P' to designate hydrogen or such a group.

The protective group preferred on the imidazole nitrogen of histidine is the benzyloxycarbonyl group but may be tosyl, dinitrophenyl, benzyl, benzyl derivative or no protective group. We use the symbol W to indicate either no protective group or any of the named derivatives.

The α-carboxylic acid group of glutamic acid is protected by a Bz group.

A coupling agent (CA) such as dicyclohexylcarbodiimide (DCC) or other coupling agent which forms peptide bonds such as diimides, azides or anhydrides or active esters may be utilized in the coupling reactions. In the attachment of asparagine the DCC coupling agent should not be used unless the asparagine has a suitable protecting group such as benzhydryl or xanthydryl, attached thereto. Without such protection DCC creates a side reaction which destroys some of the asparagine. Alternately, asparagine can be coupled, when unprotected, as an active ester.

Preparation of the Resin

The resin, which we identify by the symbol ⓇR, is a polymeric material obtained by the catalyic polymerication of styrene and divinyl benzene. Such resin is chlorinated as by the use of chloromethylmethylether and stannic chloride catalyst according to the formula:

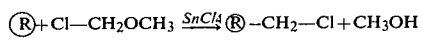

Glutamic Acid Esterification to the Resin

By our synthesis glutamic acid is first bonded to the resin. This is described by the following formula:

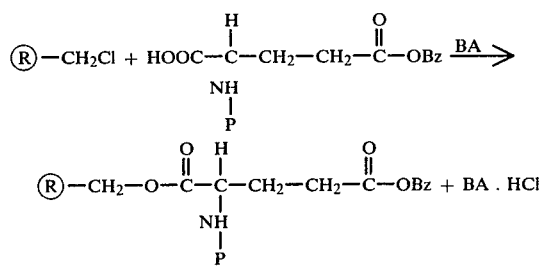

Where ℝ is polystyrene resin, BA is a suitable base such as triethylamine, diisopropylamine, or alkali metal salt, and P is an amino protective group which preferably is tertiary-butyloxycarbonyl (BOC) but may be amyloxycarbonyl (AMOC) or ortho-nitrophenylsulfenzyl (NPS), and Bz is benzyl or a benzyl derivative such as p-methoxybenzyl, p-chlorobenzyl, p-nitrobenzyl or benzydryl.

As illustrated by the above formula, the tertbutyloxycarbonyl-1-gamma-benzylglutamate is attached to the chloromethylated resin in the presence of an acid acceptor.

Deprotection and Neutralization

The deprotection of the amino function of the benzylglutamate is accomplished by the removal of the protecting group using a suitable acid such as trifluoracetic acid or hydrochloric acid. The resulting amino salt is neutralized by treatment with a strong organic base. This reaction is illustrated by the following formula:

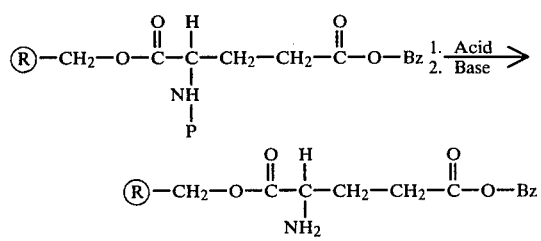

where the characters ℝ, P and Bz are the same as stated above.

For simplicity the compound

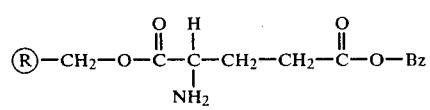

may be written as:

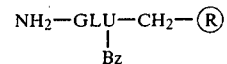

"GLU" stands for glutamate residue and ℝ and Bz are as previously designated. This simplified nomenclature places the amino terminal end on the left according to accepted nomenclature for peptides and will be used in the description of the subsequent reactions of our synthesis.

To couple the compound

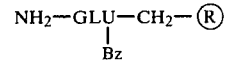

with ALA we may use BOC-L alanine which combines the amino acid to be coupled with the protecting agent and which may be purchased, as such, or may be prepared by known methods. Upon deprotection, this results in the compound:

in which the characters ℝ and Bz are as previously indicated. This is a new compound and an important link in the synthesis of compounds having hormonal activity.

This compound may then be coupled using BOC-glycine resulting, upon deprotection and neutralization in the compound:

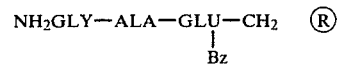

which may then be coupled with a BOC-1-asparagine-p-nitrophenyl ester resulting, upon deprotection in the compound:

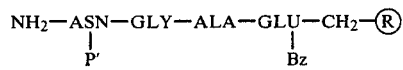

in which ℝ, Bz and P' are as previously indicated. Then the compound:

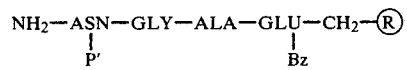

may be coupled with proline using BOC proline.

The coupling deprotection and neutralization procedures are repeated for each coupling cycle. In this way we may couple the prescribed amino acids in the sequence in which they occur in the amino acid chain of the natural ACTH structure until the final cycle in which serine is coupled at position No. 1. The preferred reactants for use in the coupling reactions are given for each position from 27 to 1 are given in the following Table No. 1.

TABLE NO. 1

| POSITION NUMBER | AMINO ACID BEING COUPLED | AMINO ACID GROUP WITH PREFERRED PROTECTANTS |
|---|---|---|
| 27 | alanine (ALA) | BOC-L-alanine |

TABLE NO. 1-continued

| POSITION NUMBER | AMINO ACID BEING COUPLED | AMINO ACID GROUP WITH PREFERRED PROTECTANTS |
|---|---|---|
| 26 | glycine (GLY) | BOC-glycine |
| 25 | Asparagine (ASN) | BOC-L-asparagine p-nitrophenyl ester |
| 24 | proline (PRO) | BOC-proline |
| 23 | tyrosine (TYR) | BOC-L-tyrosine |
| 22 | valine (VAL) | BOC-L-valine |
| 21 | lysine (LYS) | BOC-epsilon-TFA-L-lysine |
| 20 | valine (VAL) | BOC-L-valine |
| 19 | proline (PRO) | BOC-proline |
| 18 | arginine (ARG) | BOC-L-tosylarginine |
| 17 | arginine (ARG) | BOC-L-tosylarginine |
| 16 | lysine (LYS) | BOC-epsilon-TFA-L-lysine |
| 15 | lysine (LYS) | BOC-epsilon-TFA-L-lysine |
| 14 | glycine (GLY) | BOC-glycine |
| 13 | valine (VAL) | BOC-L-valine |
| 12 | proline (PRO) | BOC-L-proline |
| 11 | lysine (LYS) | BOC-epsilon-TFA-L-lysine |
| 10 | glycine (GLY) | BOC-glycine |
| 9 | tryptophane (TRY) | BOC-L-tryptophane |
| 8 | arginine (ARG) | BOC-L-tosylarginine |
| 7 | phenylalanine (PHE) | BOC-L-phenylalanine |
| 6 | histidine (HIS) | BOC-im-carbobenzyloxy-L-histidine |
| 5 | glutamic acid (GLU) | BOC-L-benzylglutamate |
| 4 | methionine (MET) | BOC-L-methionine |
| 3 | serine (SER) | BOC-O-benzyl-L-serine |
| 2 | tyrosine (TYR) | BOC-L-tyrosine |
| 1 | serine (SER) | BOC-O-benzyl-L-serine |

Further, it is important that each of the coupling reactions be complete, and we have found the Ninhydrin test, described by E. Kaiser, R. Colescott, C. D. Bossinger and P. Cook in "Anal. Biochem." 34,595,98 (1970) to be applicable to determine when the coupling reaction is sufficiently complete. If the Ninhydrin test is negative in we may proceed to the deprotection of the resin peptide and go on to the following coupling reaction. If the test is positive, we repeat the coupling step until the Ninhydrin test result is finally negative.

As indicated in Table 1 we prefer, when asparagine is being coupled, to use this amino acid in the form of its active ester, and in the coupling of tyrosine, arginine, lysine and tryptophane we prefer to include an amount of about 10% or more of dimethylformamide (DMF) for improved solubility.

When, according to the described sequence arginine is coupled at position No. 17, deprotected and neutralized the compound is:

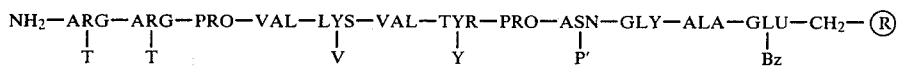

When serine is coupled at position No. 1, deprotected and neutralized, the compound becomes:

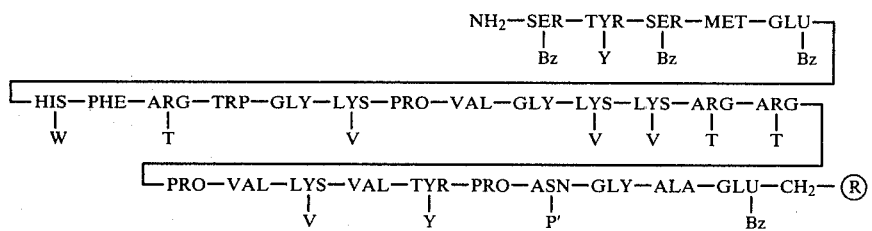

Upon completion of the coupling of the 28 amino acids and after deprotection and neutralization of serine at position No. 1, the resulting compound may be treated with hydrogen fluoride to become:

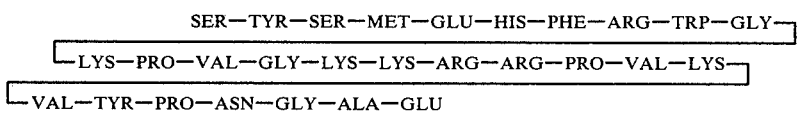

If the lysine protection is TFA then the following compound results:

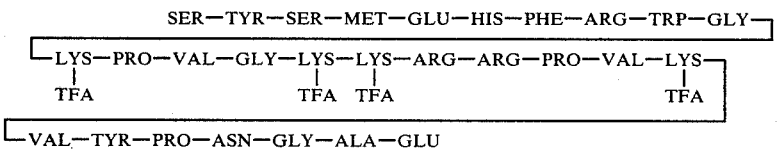

and when this compound is treated with an aqueous base such as piperidine or ammonium hydroxide to remove the TFA groups the 1-28 free peptide is generated.

The compound, free of protective groups, may be purified in accordance with known purification procedures, and will be found to have adrenocorticotropic activity.

To demonstrate our synthesis in a specific manner we set forth as follows a complete synthesis in which new compounds were made according to improvements herein described and at the last step there was obtained a compound of 28 amino acids having adrenocorticotropic activity.

SPECIFIC SYNTHESIS

EXAMPLE 1

Preparation of Chloromethyl Resin

One Kg of 2% divinylbenzene crosslinked polystyrene resin 200–400 mesh was washed with three 2 liter portions of methylene chloride. Fine particles were removed by draining the methylene chloride off the bottom each time. The resin was washed with two liters of the following solvents by suspension, stirring for ten minutes and filtration on a sintered glass Buchner: Two portions tetrahydrofuran, 2 portions water, 1 portion normal sodium hydroxide, 2 portions water, 2 portions dimethylformamide, 2 portions dioxane and 3 portions methanol. This washed resin was dried under vacuum at 60° C.

Five hundred grams of this washed polystyrene resin was stirred with 5 liters of chloromethyl methyl ether at room temperature and then the temperature was lowered to 0°–5° C. with an ice-water bath. Seventy-five grams of anhydrous stannic chloride in 925 ml ice-cold chloromethyl methyl ether was added and the mixture stirred in the ice-bath for 2 hours. The resin was filtered on a sintered glass Buchner and then washed with 2 liter portions of the following solvents: 25% water in dioxane, 25% two normal hydrochloric acid in dioxane, water and twice with methanol. The washed resin was dried under vacuum at 45°–50° C. By this method the usual chloride content is between 0.7 to 1.0 milli-equivalent per gram.

EXAMPLE 2

Preparation of Glutamic Resin

Fifty grams of chloromethylated polystyrene resin prepared as illustrated previously with a chlorine content of 0.74 milli-equivalent (meq) per gram (37 meq chlorine) and 24.9 grams BOC-L-gamma-benzylglutamate (74 meq) was stirred in 150 ml of absolute ethyl alcohol and then 9.77 ml of triethylamine (72 meq) was added and the mixture refluxed with stirring for 24 hours. The mixture was cooled, filtered on a sintered glass Buchner and washed on the Buchner with 500 ml portions of the following solvents: 2 times with 3A denatured alcohol, 2 times with dioxane, 2 times with 3A denatured alcohol, 2 times with water, 2 times with methanol. The resin was dried under vacuum at 40°–45° C. Nitrogen analysis will show values varying from about 0.50 to 0.70 meq per gram. When the BOC protecting group was removed with trifluoroacetic acid as hereinafter described and the resin titrated to determine the available terminal amine group, this sample was found to approximate 0.35 meq per gram.

EXAMPLE 3

Synthesis of the Peptide

Five grams of the glutamic resin was placed in the reaction vessel of a peptide synthesizer. The following steps were programmed for each deprotection and coupling and the amino acids were attached as set forth in Table 1.

Deprotection

2×30 ml—methylene chloride washes—2 minutes each.
30 ml 50% trifluoroacetic acid in methylene chloride—5 minutes.
(After Reaction No. 12, 1% 2-mercaptoethanol or ethanedithiol is added to the 50% trifluoroacetic acid in methylene chloride.)
3×30 ml—methylene chloride washes—2 minutes each.
2×30 ml—methanol washes—2 minutes each.
3×30 ml—chloroform washes—2 minutes each.

Neutralization

2×30 ml—10% diisopropylamine in chloroform—5 minutes each.
4×30 ml—chloroform washes—2 minutes each.

Coupling 4 millimoles of the appropriate BOC-amino acid in 20 ml of methylene chloride (or DMF mixture where required.)
4 millimoles of dicyclohexylcarbodiimide (coupling agent) in 15 ml of methylene chloride—45 minutes reaction time.
2×30 ml chloroform washes—2 minutes each.
2×30 ml methylene chloride—2 minutes each. After the final deprotection the resin was dried under vacuum. The yield was 11.8 grams.

EXAMPLE 4

Hydrogen Fluoride Cleavage

Two grams of the blocked resin peptide were placed in a Kel-F vessel with 2 ml of anisole and 10 mls of anhydrous hydrogen fluoride was added by distillation. This mixture was stirred at 0° C. for 1 hour. The hydrogen fluoride was removed by vacuum distillation, the residue washed 4 times with ethyl acetate followed by extraction with glacial acetic acid. The acetic acid extract was lyophilized to give 860 mg of a fluffy white powder. This process removes the peptide from the resin and removes all blocking groups on the difunctional amino acids except the trifluoroacetyl (TFA) blocking group of the lysine residues. Hence, this product is called TFA-peptide. The free peptide, which as biological activity, can be generated by base treatment. This is done by stirring with 1 molar piperdine or 2 N ammonium hydroxide for 3 hours. If the lysine had been protected by other functional groups the free peptide would result from the HF treatment alone.

We claim:

1. A resin peptide having the structure:

where Ⓡ is divinylbenzene crosslinked polystyrene resin and Bz is benzyl, p-methoxylbenzyl, p-chlorobenzyl, p-nitrobenzyl or benzhydryl.

2. A resin peptide have the structure:

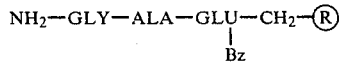

where Ⓡ is divinylbenzene crosslinked polystyrene resin and Bz is benzyl, p-methoxylbenzyl, p-chlorobenzyl, p-nitrobenzyl or benzhydryl.

3. A resin peptide having the structure:

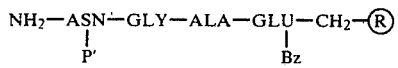

where Ⓡ is divinylbenzene crosslinked polystyrene resin and Bz is benzyl, p-methoxylbenzyl, p-chlorobenzyl, p-nitrobenzyl or benzhydryl and P' is hydrogen, xanthydryl or benzhydryl.

p-nitrobenzyl or benzhydryl; T is tosyl or nitro; V is 2-chlorocarbobenzyloxy, carbobenzyloxy, 2-bromocarbobenzyloxy, 2,4-dichlorocarbobenzyloxy or trifluoroacetyl; Y is hydrogen, benzyl or 2-bromocarbobenzyloxy; P' is hydrogen, xanthydryl or benzhydryl and W is carbobenzyloxy, tosyl, dinitrophenyl, benzyl or H.

5. a peptide having the structure:

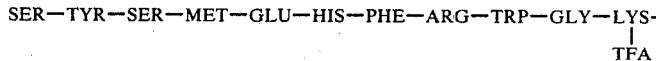
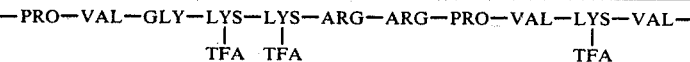
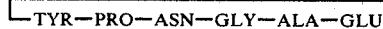

wherein: TFA is trifluoroacetyl.

6. A peptide having the structure:

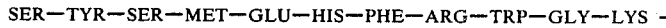
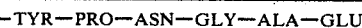

4. A resin peptide having the structure:

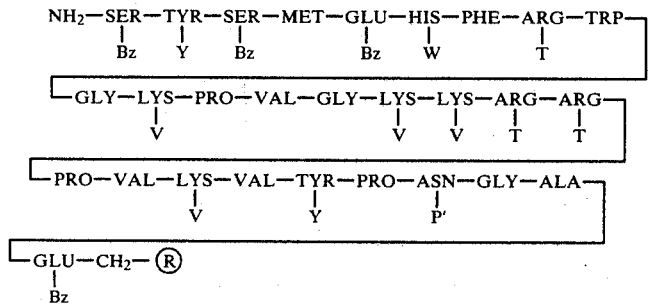

where Ⓡ is divinylbenzene crosslinked polystyrene resin; Bz is benzyl, p-methoxylbenzyl, p-chlorobenzyl,

* * * * *